United States Patent
Khamis et al.

(10) Patent No.: US 9,393,091 B2
(45) Date of Patent: Jul. 19, 2016

(54) SUTURE-LESS TISSUE FIXATION FOR IMPLANTABLE DEVICE

(75) Inventors: Chaouki A. Khamis, Edina, MN (US); James A. Alexander, Excelsior, MN (US)

(73) Assignee: Astora Women's Health, LLC, Eden Prairie, MN (US)

(*) Notice: Subject to any disclaimer, the term of this patent is extended or adjusted under 35 U.S.C. 154(b) by 936 days.

(21) Appl. No.: 12/983,077

(22) Filed: Dec. 31, 2010

(65) Prior Publication Data

US 2011/0160527 A1 Jun. 30, 2011

Related U.S. Application Data

(60) Provisional application No. 61/291,379, filed on Dec. 31, 2009.

(51) Int. Cl.
| | |
|---|---|
| *A61F 2/02* | (2006.01) |
| *A61F 2/00* | (2006.01) |
| *A61B 17/04* | (2006.01) |
| *A61B 17/00* | (2006.01) |
| *A61B 17/06* | (2006.01) |

(52) U.S. Cl.
CPC .......... *A61F 2/0045* (2013.01); *A61B 17/0401* (2013.01); *A61B 2017/00805* (2013.01); *A61B 2017/0427* (2013.01); *A61B 2017/0464* (2013.01); *A61B 2017/06176* (2013.01); *A61F 2220/0016* (2013.01)

(58) Field of Classification Search
CPC ............... A61B 17/0401; A61B 2017/00805; A61B 2017/0427; A61B 2017/06176; A61B 2017/0464; A61F 2220/0016; A61F 2/0045
USPC ............................... 600/29, 30; 128/897–899
See application file for complete search history.

(56) References Cited

U.S. PATENT DOCUMENTS

| | | | |
|---|---|---|---|
| 4,632,100 A | 12/1986 | Somers et al. |
| 4,932,962 A | 6/1990 | Yoon et al. |
| 5,013,292 A | 5/1991 | Lemay |
| 5,013,316 A | 5/1991 | Goble et al. |

(Continued)

FOREIGN PATENT DOCUMENTS

| | | |
|---|---|---|
| EP | 0650703 A1 | 6/1994 |
| EP | 0643945 A2 | 7/1994 |

(Continued)

OTHER PUBLICATIONS

Vesica® Percutaneous Bladder Neck Stabilization Kit, A New Approach to Bladder Neck Suspenison, Microvasive® Boston Scientific Corporation, 4 pages (1995).

(Continued)

*Primary Examiner* — Navin Natnithithadha
*Assistant Examiner* — Sunita Reddy
(74) *Attorney, Agent, or Firm* — Skaar Ulbrich Macari, P.A.

(57) ABSTRACT

A suture-less pelvic implant system and method is provided for treating pelvic conditions, such as incontinence or vaginal prolapse. The implant can include a fixation portion, rectangular or suture line, having a plurality of fixation elements, e.g., barbs, extending therefrom to fixate within target pelvic tissue, such as the vaginal apex. In a sacralcolpopexy, an opposing end or anchor of the implant is fixated within the sacrum or like structure to stabilize, raise, support or reposition the vaginal apex.

9 Claims, 2 Drawing Sheets

(56) References Cited

U.S. PATENT DOCUMENTS

| | | |
|---|---|---|
| 5,053,043 A | 10/1991 | Gottesman et al. |
| 5,085,661 A | 2/1992 | Moss |
| 5,112,344 A | 5/1992 | Petros |
| 5,149,329 A | 9/1992 | Richardson |
| 5,188,636 A * | 2/1993 | Fedotov .................. 606/144 |
| 5,203,864 A | 4/1993 | Phillips |
| 5,234,438 A | 8/1993 | Semrad |
| 5,256,133 A | 10/1993 | Spitz |
| 5,268,001 A | 12/1993 | Nicholson et al. |
| 5,281,237 A | 1/1994 | Gimpelson |
| 5,328,077 A | 7/1994 | Lou |
| 5,337,736 A | 8/1994 | Reddy |
| 5,354,292 A | 10/1994 | Braeuer et al. |
| 5,368,595 A | 11/1994 | Lewis |
| 5,370,650 A | 12/1994 | Tovey et al. |
| 5,376,097 A | 12/1994 | Phillips |
| 5,403,328 A | 4/1995 | Shallman |
| 5,439,467 A | 8/1995 | Benderev et al. |
| 5,474,518 A | 12/1995 | Farrer Velazquez |
| 5,474,543 A | 12/1995 | McKay |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,582,188 A | 12/1996 | Benderev et al. |
| 5,584,860 A | 12/1996 | Goble et al. |
| 5,591,163 A | 1/1997 | Thompson |
| 5,591,206 A | 1/1997 | Moufarrege |
| 5,611,515 A | 3/1997 | Benderev et al. |
| 5,674,247 A | 10/1997 | Sohn |
| 5,683,349 A | 11/1997 | Makower et al. |
| 5,690,655 A | 11/1997 | Hart et al. |
| 5,697,931 A | 12/1997 | Thompson |
| 5,725,529 A | 3/1998 | Nicholson et al. |
| 5,725,541 A | 3/1998 | Anspach, III et al. |
| 5,741,282 A | 4/1998 | Anspach, III et al. |
| 5,782,862 A | 7/1998 | Bonuttie |
| 5,873,891 A | 2/1999 | Sohn |
| 5,899,909 A | 5/1999 | Claren et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,997,554 A | 12/1999 | Thompson |
| 6,030,393 A | 2/2000 | Corlew |
| 6,042,583 A | 3/2000 | Thompson et al. |
| 6,048,351 A | 4/2000 | Gordon et al. |
| 6,053,935 A | 4/2000 | Brenneman et al. |
| 6,056,688 A | 5/2000 | Benderev et al. |
| 6,099,538 A | 8/2000 | Moses |
| 6,099,551 A | 8/2000 | Gabbay |
| 6,168,611 B1 | 1/2001 | Rizvi |
| 6,241,736 B1 | 6/2001 | Sater et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,319,272 B1 | 11/2001 | Brenneman |
| 6,322,492 B1 | 11/2001 | Kovac |
| 6,328,744 B1 | 12/2001 | Harari et al. |
| 6,334,446 B1 | 1/2002 | Beyar |
| 6,382,214 B1 | 5/2002 | Raz et al. |
| 6,406,423 B1 | 6/2002 | Scetbon |
| 6,406,480 B1 | 6/2002 | Beyar et al. |
| 6,423,072 B1 | 7/2002 | Zappala |
| 6,423,080 B1 | 7/2002 | Gellman et al. |
| 6,440,154 B2 | 8/2002 | Gellman et al. |
| 6,451,024 B1 | 9/2002 | Thompson et al. |
| 6,454,778 B2 | 9/2002 | Kortenbach |
| 6,475,139 B1 | 11/2002 | Miller |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,575,897 B1 * | 6/2003 | Ory et al. .................. 600/30 |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,602,260 B2 | 8/2003 | Harari et al. |
| 6,612,977 B2 | 9/2003 | Staskin |
| 6,635,058 B2 | 10/2003 | Beyar et al. |
| 6,638,210 B2 | 10/2003 | Berger |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,695,855 B1 * | 2/2004 | Gaston .................. 606/151 |
| 6,702,827 B1 | 3/2004 | Lund |
| 6,730,110 B1 | 5/2004 | Harari et al. |
| 6,746,455 B2 | 6/2004 | Beyar et al. |
| 6,752,814 B2 | 6/2004 | Gellman et al. |
| 6,802,807 B2 | 10/2004 | Anderson |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,003 B2 | 6/2005 | Anderson et al. |
| 6,932,759 B2 | 8/2005 | Kammerer |
| 6,936,052 B2 | 8/2005 | Gellman et al. |
| 6,971,986 B2 | 12/2005 | Staskin et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,070,556 B2 | 7/2006 | Anderson et al. |
| 7,083,637 B1 | 8/2006 | Tannhauser |
| 7,087,059 B2 | 8/2006 | Harari et al. |
| 7,112,171 B2 | 9/2006 | Rocheleau et al. |
| 7,121,997 B2 | 10/2006 | Kammerer et al. |
| 7,131,943 B2 | 11/2006 | Kammerer |
| 7,223,229 B2 | 5/2007 | Inman et al. |
| 7,226,407 B2 | 6/2007 | Kammerer |
| 7,226,408 B2 | 6/2007 | Harari et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,267,645 B2 | 9/2007 | Anderson et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal |
| 7,494,495 B2 | 2/2009 | Delorme et al. |
| 7,500,945 B2 | 3/2009 | Cox |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Priewe et al. |
| 7,588,598 B2 | 9/2009 | Delorme et al. |
| 7,601,118 B2 | 10/2009 | Smith et al. |
| 7,614,999 B2 | 11/2009 | Gellman et al. |
| 7,621,865 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |

(56) References Cited

U.S. PATENT DOCUMENTS

| | | |
|---|---|---|
| 7,691,052 B2 | 4/2010 | Gellman et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,828,715 B2 | 11/2010 | Haverfield |
| 7,905,825 B2 | 3/2011 | Arnal et al. |
| 7,909,753 B1 | 3/2011 | Ogdahl et al. |
| 7,914,437 B2 | 3/2011 | Gozzi |
| 2001/0000533 A1 | 4/2001 | Kovac |
| 2001/0018549 A1 | 8/2001 | Scetbon |
| 2001/0027321 A1 | 10/2001 | Gellman et al. |
| 2001/0041895 A1 | 11/2001 | Beyar et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1* | 3/2002 | Thierfelder et al. ............ 600/37 |
| 2002/0035369 A1 | 3/2002 | Beyar et al. |
| 2002/0038119 A1 | 3/2002 | Weber et al. |
| 2002/0038132 A1 | 3/2002 | Abrams |
| 2002/0050277 A1 | 5/2002 | Beyar |
| 2002/0055748 A1 | 5/2002 | Gellman et al. |
| 2002/0058959 A1 | 5/2002 | Gellman et al. |
| 2002/0068948 A1 | 6/2002 | Stormby et al. |
| 2002/0077526 A1 | 6/2002 | Kammerer et al. |
| 2002/0091373 A1 | 7/2002 | Berger |
| 2002/0095064 A1 | 7/2002 | Beyar |
| 2002/0095163 A1 | 7/2002 | Beyer et al. |
| 2002/0095181 A1 | 7/2002 | Beyar |
| 2002/0107525 A1 | 8/2002 | Harari et al. |
| 2002/0128681 A1 | 9/2002 | Broome et al. |
| 2002/0147382 A1 | 10/2002 | Neisz et al. |
| 2002/0151762 A1 | 10/2002 | Rocheleau |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0171644 A1 | 9/2003 | Anderson et al. |
| 2003/0176875 A1 | 9/2003 | Anderson |
| 2003/0212305 A1 | 11/2003 | Anderson et al. |
| 2003/0225424 A1 | 12/2003 | Benderev |
| 2004/0015057 A1 | 1/2004 | Rocheleau et al. |
| 2004/0039453 A1 | 2/2004 | Anderson et al. |
| 2004/0087970 A1 | 5/2004 | Chu et al. |
| 2004/0144395 A1* | 7/2004 | Evans et al. ................ 128/885 |
| 2004/0193215 A1 | 9/2004 | Harari et al. |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004426 A1 | 1/2005 | Raz et al. |
| 2005/0004576 A1 | 1/2005 | Benderev |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0250977 A1 | 11/2005 | Montpetit et al. |
| 2005/0256366 A1 | 11/2005 | Chu |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0195007 A1 | 8/2006 | Anderson |
| 2006/0195010 A1 | 8/2006 | Arnal et al. |
| 2006/0195011 A1 | 8/2006 | Arnal |
| 2006/0217589 A1 | 9/2006 | Wam et al. |
| 2006/0229493 A1 | 10/2006 | Weiser et al. |
| 2006/0229596 A1 | 10/2006 | Weiser et al. |
| 2006/0235262 A1 | 10/2006 | Arnal et al. |
| 2006/0260618 A1 | 11/2006 | Hodroff et al. |
| 2006/0287571 A1 | 12/2006 | Gozzi |
| 2007/0010830 A1 | 1/2007 | Gellman et al. |
| 2007/0015953 A1 | 1/2007 | MacLean |
| 2007/0078295 A1 | 4/2007 | landgrebe |
| 2007/0123915 A1* | 5/2007 | Kammerer et al. ........... 606/151 |
| 2007/0173864 A1 | 7/2007 | Chu |
| 2008/0039678 A1 | 2/2008 | Montpetit et al. |
| 2008/0103351 A1 | 5/2008 | Montpetit et al. |
| 2008/0132754 A1 | 6/2008 | Thierfelder et al. |
| 2008/0140218 A1 | 6/2008 | Staskin et al. |
| 2008/0207989 A1 | 8/2008 | Kaleta et al. |
| 2008/0300607 A1 | 12/2008 | Meade et al. |
| 2009/0012592 A1 | 1/2009 | Ogdahl et al. |
| 2009/0137864 A1 | 5/2009 | Cox et al. |
| 2009/0156891 A1 | 6/2009 | Heys et al. |
| 2009/0182190 A1 | 7/2009 | Dann |
| 2009/0221867 A1 | 9/2009 | Ogdahl et al. |
| 2009/0221868 A1 | 9/2009 | Evans |
| 2009/0240104 A1 | 9/2009 | Ogdahl et al. |
| 2010/0105979 A1 | 4/2010 | Otte et al. |
| 2010/0152528 A1 | 6/2010 | Chapmenan et al. |
| 2010/0168505 A1 | 7/2010 | Inman et al. |
| 2010/0256442 A1 | 10/2010 | Ogdahl et al. |
| 2010/0261952 A1 | 10/2010 | Montpetit et al. |
| 2010/0305394 A1* | 12/2010 | Rosenblatt ....................... 600/30 |
| 2011/0034759 A1 | 2/2011 | Ogdahl et al. |
| 2011/0082328 A1 | 4/2011 | Gozzi et al. |
| 2011/0124954 A1* | 5/2011 | Ogdahl .................. A61F 2/0045 600/30 |
| 2012/0108894 A1* | 5/2012 | Young et al. .................... 600/37 |
| 2014/0128664 A1* | 5/2014 | Ogdahl .................. A61F 2/0045 600/30 |

FOREIGN PATENT DOCUMENTS

| | | |
|---|---|---|
| EP | 0632999 A1 | 1/1995 |
| WO | WO9310715 A1 | 6/1993 |
| WO | WO9319678 A2 | 10/1993 |
| WO | WO9511631 A1 | 5/1995 |
| WO | WO9525469 A1 | 9/1995 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9842261 A1 | 10/1998 |
| WO | WO9853746 A1 | 12/1998 |
| WO | WO9937216 A1 | 7/1999 |
| WO | WO9937217 A1 | 7/1999 |
| WO | WO9952450 A1 | 10/1999 |
| WO | WO9953844 A1 | 10/1999 |
| WO | WO9958074 A2 | 11/1999 |
| WO | WO9959477 A1 | 11/1999 |
| WO | WO0013601 A1 | 3/2000 |
| WO | WO0030556 A1 | 6/2000 |
| WO | WO0057796 A1 | 10/2000 |
| WO | WO02062237 A1 | 8/2002 |
| WO | WO02071953 A2 | 9/2002 |
| WO | WO03034939 A1 | 5/2003 |
| WO | WO03075792 A1 | 9/2003 |
| WO | WO2004034912 A1 | 4/2004 |
| WO | WO2005004727 A1 | 1/2005 |
| WO | WO2005079702 A1 | 9/2005 |
| WO | WO2007002012 A1 | 1/2007 |
| WO | WO2007002071 A1 | 1/2007 |
| WO | WO2007027592 A2 | 3/2007 |
| WO | WO2007059199 A2 | 5/2007 |
| WO | WO2007097994 | 8/2007 |
| WO | WO2007146784 A2 | 12/2007 |
| WO | WO2007149348 A2 | 12/2007 |
| WO | WO2008057261 A2 | 10/2008 |

(56) References Cited

FOREIGN PATENT DOCUMENTS

| WO | WO2008124056 A1 | 10/2008 |
| WO | WO2009005714 A2 | 1/2009 |
| WO | WO2009017680 A2 | 2/2009 |

OTHER PUBLICATIONS

Benderev, Theodore V., MD, A Modified Percutaneous Outpatient Bladder Neck Suspension System, Journal of Urology, vol. 152, pp. 2316-2320 (Dec. 1994).

Capio™ CL—Transvaginal Suture Capturing Device—Transvaginal Suture Fixation to Cooper's Ligament for Sling Procedures, Boston Scientific, Microvasive®, 8 pages, (2002).

Kovac, S. Robert, et al, Pubic Bone Suburethral Stabilization Sling: A Long Term Cure for SUI?, Contemporary OB/GYN, 10 pages (Feb. 1998).

Precision Tack, The Precise Approach to Transvaginal Sling Procedures, Boston Scientific, 1998, 4pp.

Precision Twist, Low Profile design for Precise Anchor Placement, Boston Scientific Microvasive, 2001 2 pp.

Sanz, Luis E. et al., Modification of Abdominal Sacrocolpopexy Using a Suture Anchor System, The Journal of Reproductive Medicine, vol. 48, n. 7, pp. 496-500 (Jul. 2003).

Vesica Sling Kit, Microvasive Boston Scientific, 1997, 6pp.

* cited by examiner

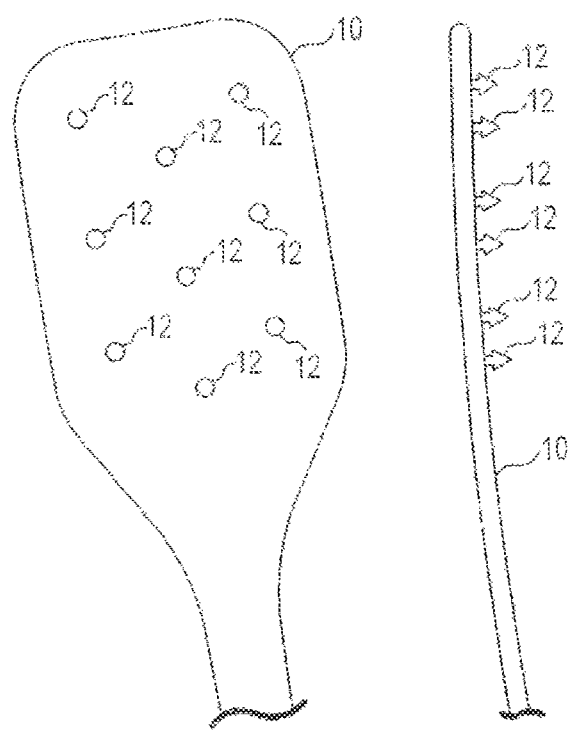
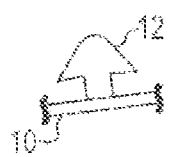  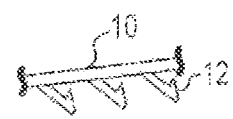
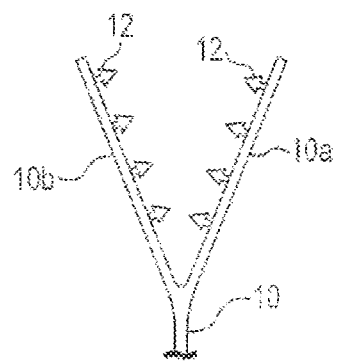

SUTURE-LESS TISSUE FIXATION FOR IMPLANTABLE DEVICE

PRIORITY

This Application claims priority to and the benefit of U.S. Provisional Application No. 61/291,379, filed Dec. 31, 2009, which is incorporated herein by reference in its entirety.

FIELD OF THE INVENTION

The present invention relates generally to surgical methods and apparatus and, more specifically, to suture-less surgically implantable mesh or sling devices and methods for forming and using the same.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

Conventional implantation of pelvic devices requires sutures. For example, in the current Sacrocolpopexy (SCP) procedure, the physician may place approximately between 5 and 16 sutures to secure the mesh to the vaginal apex. Placing these sutures is a time consuming task for the surgeon and prolongs the procedure for the patient.

There is a desire to provide an device and method for implanting a mesh implant without the use of sutures.

SUMMARY OF THE INVENTION

The present invention provides suture-less pelvic mesh implants or sling devices and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

The fixation mechanism and method in accordance with certain exemplary embodiments utilize a mesh or a line of suture material with molded or otherwise provided anchors, hooks or fixation elements, such as barbs. These fixation elements can be depth limited to prevent complete puncture or penetration of the target tissue, such as the vagina. An implantation device is also described and provides a repeatable load application to properly reach and seat the hooks.

The implant can include a fixation portion, rectangular or suture line, having a plurality of the fixation elements, e.g., barbs, extending therefrom to fixate within target pelvic tissue, such as the vaginal apex. In a sacralcolpopexy, an opposing end or anchor of the implant is fixated within the sacrum or like structure to stabilize, raise, support or reposition the vaginal apex.

BRIEF DESCRIPTION OF THE DRAWINGS

FIG. 1 is a front view of an implant having extending fixation elements in accordance with embodiments of the present invention.

FIG. 2 is a side view of the implant of FIG. 1.

FIGS. 3-5 show various implant fixation element configurations and designs in accordance with embodiments of the present invention.

FIG. 6 is a side view of a generally Y-shaped implant having extending fixation elements in accordance with embodiments of the present invention.

DETAILED DESCRIPTION OF PREFERRED EMBODIMENTS

Figure 7:
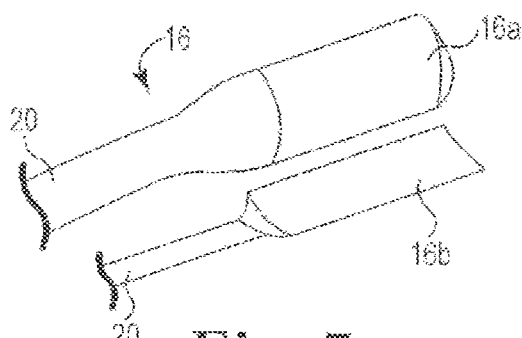
FIG. 7 is a partial perspective view of an insertion and fixation tool in accordance with embodiments of the present invention.

The present invention is generally directed to systems and methods of deploying and attaching an implant 10. In various embodiments, the implant 10 will be adapted to provide fixation to the apex of the vagina to the sacrum or other known anatomical structures, such as that performed in a sacralcolpopexy procedure, to reposition, support or otherwise address positioning or support of the apex. The dimensions of the implant or its corresponding portions will depend upon a variety of factors including the intended surgical uses.

For a sacralcolpopexy procedure, the dimensions of the implant 10 are at least sufficient to extend from the sacrum to the vaginal apex with additional size to account for the imprecision associated with the range of human anatomy sizes and for a small amount of slack. In one embodiment, the maximum width of the implantable article is between about 1 and 6 centimeters, the overall length is between about 10 and 20 cm, and the thickness is between about 0.020 and 0.1 inches. Other dimensions are also envisioned for use with the present invention in accordance with the description and details of the fixation devices and methods provided herein. Certain embodiments of the implant 10 can be constructed of a generally flexible or semi-flexible polymer or mesh material. Relatively flexible implants 10 can be employed to contour or conform to the shape of the target fixation tissue, e.g., apex of the vagina.

Various systems, devices and methods are envisioned for use with the present invention, including those disclosed in U.S. Pat. Nos. 7,500,945, 7,407,480, 7,351,197, 7,347,812, 7,303,525, 7,025,063, 6,884,212, 6,691,711, 6,648,921, 6,612,977, and 6,541,828, International Patent Publication Nos. WO 2008/057261 and WO 2007/097994, and U.S. Patent Publication Nos. 2008/0132754, 2002/151762 and 2002/147382. Accordingly, the above-identified disclosures and references are fully incorporated herein by reference in their entirety.

This present invention includes tools and methods for suture-less approaches to tissue fixation—e.g., fixation to the vagina or vaginal apex. Namely, while sutures may be included to construct one or more portions of the implant, the sutures are not sewn to the tissue T as performed with conventional fixation methods. Conversely, embodiments of the present invention are directed to fixation of the implant 10, e.g., mesh implant, to vaginal apex tissue T without suturing. However, it should be understood that the present invention is applicable to the suture-less implantation of slings or mesh implants of any size or shape, and for any condition to be addressed by such an implant.

The fixation system and method in accordance with certain exemplary embodiments utilizes a mesh or a line of suture material with molded in, or otherwise attached or provided, anchor or hook-like fixation elements, such as barbs. These fixation elements can be depth limited to prevent a complete puncture or penetration of the tissue T, such as the vagina.

Sutures can be threaded onto or include the barbs in certain embodiments to further limit the amount of material required for fixation to the tissue T as compared to the other implants disclosed herein.

Figure 15:
FIG. 15 shows a barb or fixation element in accordance with embodiments of the present invention.

Referring now to FIGS. 1-6, the implant 10 includes a plurality of fixation elements or barbs 12 extending outwardly from one of the generally planar surfaces of the implant 10. These barbs 12 have a generally arrow-headed shape to facilitate insertion into the patient tissue and retention in the tissue (e.g., resistance to pullout). The barbs 12 take on a wide variety of shapes to facilitate fixation, while beneficially reducing the amount of force required to push the barbs 12 into the target tissue site. The barbs 12 can be angled, rounded, include one or more tines, and can include various other protuberances and features to facilitate fixation, e.g., FIGS. 3-5. In FIG. 15, a circular or partially circular barb element 12 includes a curved or angled hook to facilitate tissue fixation with corresponding rotation.

As shown in FIG. 6, the implant 10 can be generally defined in a Y-shaped form to provide better fixation to tissue T, such as the vaginal apex. For instance, a first portion 10a of the implant 10 can be affixed to the anterior portion of the apex, while a second portion 10b of the implant 10 can be affixed to the posterior portion of the apex. An opposing end of the implant 10 extends out for fixation within the pelvic cavity to tension or support the vagina or apex. For instance, the opposing end anchor described herein can be affixed or attached at or proximate the sacrum, or other tissue or anatomical structures such as the sacrospinous ligament, obturator membrane, and like tissues known to those of ordinary skill in the art for fixation in a sacralcolpopexy or similar procedure.

Figure 8:
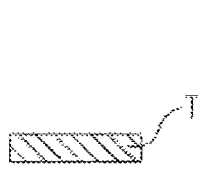
FIGS. 8-10 show various stages of deploying or inserting one or more fixation elements into tissue in accordance with embodiments of the present invention.
Figure 9:
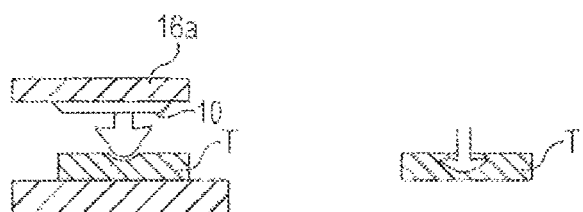
Figure 10:
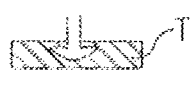

Again, the barbs can be sized and shaped to prevent complete penetration through the vaginal wall or apex T. FIGS. 8-10 depict the insertion of the barbs or tissue hooks into the patient tissue T, e.g., using a fixation tool 16. The barbs also resist shear forces from moving the mesh or implant 10 once fixated.

The fixation tool 16, such as shown in FIG. 7 can be provided to facilitate insertion of the barbs 12 into the patient tissue. Such a tool 16 ensures that a repeatable load is applied by giving the operator feedback in the vagina that the correct pressure has been reached and the anchors 12 are properly seated or engaged. The fixation tool 16 can include two opposing hingable jaw portions 16a, 16b. A handle 20 of the fixation tool can be operated to actuate the jaw portions 16a, 16b together to press the barbs 12 into the respective target tissue. The handle 20 or another portion of the fixation tool 16 can click when fixation is complete, thereby providing audible and tactile feedback to the user.

In various embodiments, a vaginal incision can be made such that at least one of the jaw portion (16a) is positionable on a first side of the vaginal wall or apex and the second jaw portion (16b) is placed on the opposing side of the vaginal wall or apex. As such one jaw portion can be positioned outside the vagina and the other jaw portion inside the vagina to facilitate squeezing of the tool 16 to engage the barbs 12 into the tissue. In other embodiments, the fixation tool 16 can be employed to fixate the barbs within the tissue without requiring a vaginal incision.

Figure 11:
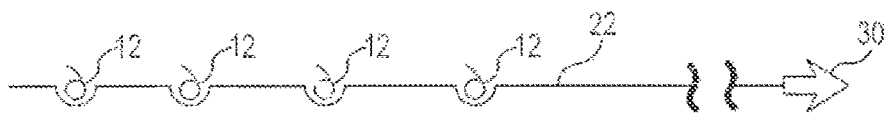
FIG. 11 shows a side view of a suture line implant including fixation elements and an opposing end anchor in accordance with embodiments of the present invention.
Figure 12:
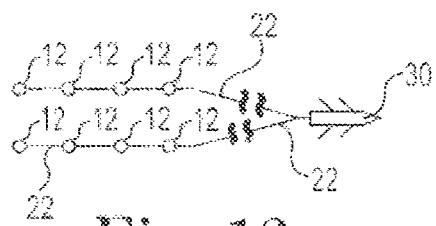
FIG. 12 shows a side view of a Y-shaped suture line implant including fixation elements and an opposing end anchor in accordance with embodiments of the present invention.

Referring to FIGS. 11-12, a line or series of fixation elements or barbs 12 is shown along a suture line 22. The suture line 22 can include the previously disclosed opposing anchor 30. The opposing anchor 30 can include various tines or like features to facilitate fixation to the sacrum or other like tissue or anatomical structure within the pelvic cavity. The barbs 12 can be integrated with, attached or otherwise provided with the suture 22 at spaced locations along the length of the suture 22. In one embodiment, the barbs 12 can include one or more apertures 24 or indents adapted to receive and secure to a portion of the suture 22. FIG. 12 shows an implant 10 having at least two distinct suture lines 22 extending from the anchor 30 to form a generally Y-shaped for apex fixation.

Figure 13:
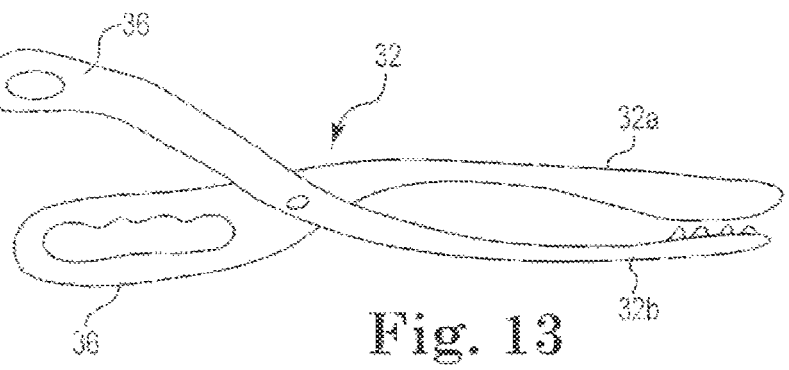
FIG. 13 shows a delivery and fixation tool in accordance with embodiments of the present invention.

In certain embodiments, the sutured line of fixation elements or barbs 12 can be separately fixated to the tissue using the insertion and fixation tool 32 of FIG. 13. The tool 32 has an application or jaw portion (32a, 32b) where the fixation element assembly is retained (and optionally covered to facilitate movement through tissue). The tool 32 is then used to line up the fixation element assembly 10, 22, squeeze and engage it with the mesh and patient tissue, thereby securing the implant 10 to the tissue. The tool 32 and fixation element assembly 10, 22 can be sized and shaped according to the particular application. Further, the tool 32 can include one or more pivoting handle portions 36.

Figure 14:
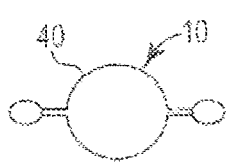
FIG. 14 shows a clasp or clamp implant or implant portion in accordance with embodiments of the present invention.

Referring to FIG. 14, the implant can be constructed as or include a clasp or clamp device 40. Such a device 40 can be adapted to clasp around a portion of the vagina, such as the apex, to capture and fixation to the vagina a sacralcolpopexy procedure. Such clamps 40 can be used in conjunction with or as an alternative to the previous fixation elements described herein. The device 40 can be connected or extend to the anchor 30 described herein for fixation to the sacrum or like anatomical structure.

Various additional fixation element 12 and barb designs can be employed without departing from the scope of the present invention. For example, various motions can be employed with various alternative elements 12 to actuate fixation within the tissue (rotating, pivoting, pushing, sliding, etc.). The fixation elements 12 can be varied in size and shape within the same application or assembly. The fixation elements 12 can also have multiple retention features on each element 12.

The fixation elements or barbs 12 be constructed or formed of any suitable material, including various compatible metals and polymers. Examples include polypropylene, polyethylene, fluoropolymers or like compatible materials.

Numerous modifications and variations of the present invention are possible in light of the teachings herein. It is therefore to be understood that within the scope of the appended claims, the invention may be practiced other than as specifically described herein.

The invention claimed is:

1. A method of performing a sacralcolpopexy procedure in a patient, comprising:
   providing a generally flexible implant having an implant thickness and a generally planar first surface having a plurality of spaced fixation elements extending transversely and longitudinally from the generally planar first surface, each of the spaced fixation elements oriented generally parallel to one another,
   wherein the plurality of fixation elements are generally arrow-shaped barb members,
   wherein providing an implant includes providing an implant having first and second fixation portions defining a generally Y-shaped implant having the plurality of fixation elements extending from the first and second fixation portions; and
   wherein an end anchor is provided distal to and operably coupled with the implant; providing a fixation tool having first and second jaw portions;
   inserting the fixation tool within a pelvic cavity of the patient;
   positioning the vaginal tissue intermediate the plurality of fixation elements and the first jaw portion of the fixation tool by positioning the fixation tool;
   bringing the first and second jaw portions toward each other to force the plurality of fixation elements into the vaginal tissue by engaging the fixation tool; and
   engaging the end anchor of the implant in pelvic region tissue distinct from the vaginal tissue.

2. The method of claim 1, wherein forcing the plurality of fixation elements into the vaginal tissue includes forcing the plurality of fixation elements into an apex portion of the vagina.

3. The method of claim 1, further including incising a vaginal wall portion to provide access for at least one of the first and second jaw portions of the fixation tool outside the vaginal wall.

4. The method of claim 1, wherein the first and second jaw portions of the fixation tool are hingably connected.

5. The method of claim 1, wherein forcing the plurality of fixation elements into the vaginal tissue includes forcing the plurality of fixation elements into the vaginal tissue without completely penetrating through the vaginal tissue.

6. The method of claim 1, wherein engaging the end anchor of the implant in tissue other than the vaginal tissue includes engaging the end anchor of the implant in the sacrum.

7. The method of claim 1, wherein providing an implant includes providing an implant constructed at least in part of a suture line.

8. The method of claim 1, wherein the plurality of fixation elements are angled barb members.

9. The method of claim 1, wherein the plurality of fixation elements are curved barb members.

* * * * *